(12) United States Patent
Robertson, Jr. et al.

(10) Patent No.: US 8,189,199 B2
(45) Date of Patent: May 29, 2012

(54) DUAL SAMPLE MODE SPECTROPHOTOMETER

(75) Inventors: Charles W. Robertson, Jr., Centreville, DE (US); Catherine T. Williams, Kennett Square, PA (US); Jonathan Pundt, Verona, WI (US)

(73) Assignee: Nanodrop Technologies, LLC, Wilmington, DE (US)

( * ) Notice: Subject to any disclaimer, the term of this patent is extended or adjusted under 35 U.S.C. 154(b) by 443 days.

(21) Appl. No.: 12/572,143

(22) Filed: Oct. 1, 2009

(65) Prior Publication Data

US 2010/0085568 A1    Apr. 8, 2010

Related U.S. Application Data

(60) Provisional application No. 61/102,728, filed on Oct. 3, 2008.

(51) Int. Cl.
*G01N 21/00* (2006.01)
*G01N 1/10* (2006.01)

(52) U.S. Cl. ........................................ 356/440; 356/246

(58) Field of Classification Search .................. 356/440, 356/246
See application file for complete search history.

(56) References Cited

U.S. PATENT DOCUMENTS

| | | | |
|---|---|---|---|
| 3,977,794 | A | 8/1976 | Liedholz |
| 5,739,432 | A | 4/1998 | Sinha |
| 5,774,209 | A | 6/1998 | Shestock |
| 6,628,382 | B2 | 9/2003 | Robertson |
| 6,809,826 | B2 | 10/2004 | Robertson |
| 7,397,036 | B2 | 7/2008 | Robertson et al. |
| 2003/0003591 | A1 | 1/2003 | LaCourt et al. |
| 2006/0077390 | A1 | 4/2006 | Kralik |
| 2006/0087650 | A1 | 4/2006 | Shen |
| 2006/0109468 | A1 | 5/2006 | Evans |

*Primary Examiner* — Gregory J Toatley
*Assistant Examiner* — Amanda Merlino
(74) *Attorney, Agent, or Firm* — Michael C. Staggs (57) ABSTRACT

A dual-mode method and apparatus of selectively measuring samples in either a vessel or as a surface tension retained sample held between two opposing pedestals is introduced. In either configuration, such modes further contain optical paths from a source system through a small-volume or large-volume sample to a spectrometer based system. Such a system enables a user to measure samples with absorbances ranging from about 0.005 up to about 2.0 Absorbance Units for any given wavelength.

28 Claims, 4 Drawing Sheets

FIG. 4

DUAL SAMPLE MODE SPECTROPHOTOMETER

RELATED APPLICATION

This application claims the benefit of U.S. Provisional Application No. 61/102,728, filed Oct. 3, 2008, entitled: "Dual Sample Mode Spectrophotometer," which is incorporated herein by this reference.

FIELD OF THE INVENTION

The present invention relates to the fields of spectrophotometers and their use in optically quantitating and/or characterizing liquids and solutions. More particularly, the present invention is directed to spectrophotometers and related instruments for characterizing optical transmission and absorbance of large-volume as well as small-volume samples having optical path lengths from about 10 microns up to about 25 millimeters.

BACKGROUND OF THE INVENTION

Liquids, mixtures, solutions and reacting mixtures are often characterized using optical techniques such as photometry, spectrophotometry, fluorometry, or spectrofluorometry.

In particular, sampling techniques used in UV-Visible spectrophotometry can include using cuvettes configured with one or more optical windows and a fixed optical path length so as to hold a sample in a semi-closed way. Such a cuvette-based vessel method is typically incorporated by pipetting a sample into such a vessel that has either a 10 mm or a 2 mm path length. The method itself, is limited for most biological samples since cuvettes most often require a mL sample, which is often discarded after measurements. Large sample volume and loss can thus be problematic for valuable biological samples which are often of limited quantities. Moreover, directed samples into such cuvettes can produce air-interface bubble interfaces in the optical measurement path, which can produce measurement errors. Additionally, a path-length of 2 mm or 10 mm limits the sample concentration that may be measured to 1000 ng/ml for a DNA/RNA sample due to the limited dynamic range of absorbance of most spectrophotometers.

To overcome the aforementioned difficulties of handling biological samples of limited quantities, and/or of which requires dilution and/or which has contamination issues, other techniques, such as those similarly disclosed in U.S. Pat. Nos. 6,809,826 and 6,628,382, which are incorporated herein by reference in its entirety, have been developed to enable a user to investigate path lengths in the range from about 0.2 to 2 mm and generate absorbance values that can be easily corrected to using a cuvette-based techniques. According to the teachings in the aforementioned patents, a smaller sample volume, which is incapable of being investigated in a cuvette-based apparatus, is held between two opposing substantially parallel surfaces by interfacial tension and one surface is controllably moved toward and/or away from the other. To provide and transmit light through the droplet for measurement, and to collect light for measurement, at least one of the surfaces may have a portion of optical measurement quality. This may be accomplished by providing at least a portion of at least one of the surfaces as a polished end of an optical fiber, each such optical fiber preferably finished flush with the surrounding surface portion. Conveniently, such surrounding surface portion may comprise the surface of an end of a standard fiber optic connector or other fiber holder.

However, while the aforementioned interfacial tension techniques have beneficial aspects over cuvette-based methods, a need urgently exists for an integrated spectroscopic apparatus that is configured to interrogate small sample volumes while additionally capable of handling larger sample volumes configured in vessels having measurement lengths of up to about 25 mm, more often of up to about 10 mm. The reasoning is that such an integrated apparatus and corresponding methods thereof enable a user to cross-calibrate measurements within the instrument itself in addition to cross-calibrating and interfacing with other existing conventional instruments and methods currently in the industry. Accordingly, the present invention is directed to such a need.

SUMMARY OF THE INVENTION

The present invention is directed to an optical apparatus that can selectively measure samples in either a vessel (e.g., a cuvette) and/or in a surface tension retained mode, e.g., a sample contained via surface tension between two opposing pedestals, wherein each mode comprises an optical path from a source system, through the sample, and eventually to a spectrometer based system to enable the capability of measuring absorbances from about 0.005 up to about 2.0 Absorbance Units for any given path length.

Accordingly, an aspect of the present invention is directed to a dual-mode spectrophotometer that includes: a first pedestal surface coupled to a first optical conduit having a transmitting end; a base plate; a second pedestal surface mechanically coupled to the base plate and configured to receive a first liquid sample, the second pedestal surface being coupled to a second optical conduit having a receiving end, wherein the second pedestal further is operable so as to adjust a separation between the first and the second pedestal at a variable distance (P) to pull the first liquid sample into a column so as to be contained by surface tension, thereby providing an optical path with the transmitting end of the first optical conduit and the receiving end of the second optical conduit for photometric or spectrometric measurement; a vessel holder configured with a recessed guide means, the vessel holder configured to be removably coupled to the base plate, and; a sample vessel configured to be resiliently secured within the recessed guide means, the sample vessel having a second liquid sample therein and configured with at least two window means therein, thereby also providing an optical path for photometric or spectrometric measurement.

Another aspect of the present invention is directed to a dual-mode spectrophotometer method for measuring an optical property of a sample contained in either a surface tension mode or contained in a cuvette, including: providing a first pedestal surface coupled to a first optical conduit having a transmitting end; placing a first sample on a second pedestal surface mechanically coupled to a base plate, the second pedestal surface being coupled to an optical conduit having a receiving end, wherein the second pedestal surface is further operable so as to adjust a separation between the first and the second pedestal surfaces at a variable distance (P) to pull the first liquid sample into a column so as to be contained by surface tension, thereby providing an optical path with the transmitting end of the first optical conduit and the receiving end of the second optical conduit for photometric or spectrometric measurements; providing a vessel holder configured with a recessed guide means, the vessel holder configured to be removably coupled to the base plate, and; providing a sample vessel configured to be resiliently secured within the recessed guide means, the sample vessel having a second liquid sample disposed therein and configured with at least two window means therein, thereby also providing an optical path for photometric or spectrometric measurements, wherein desired photometric or spectrometric measurements can be provided on the sample held in surface tension and/or on the second liquid sample disposed therein the vessel.

DETAILED DESCRIPTION OF EMBODIMENTS

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

Moreover, unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

The present invention is directed to an optical instrument and method for measuring an analyte in a sample, which includes fluorometric, photometric, spectrophotometric and/or spectrofluorometric analysis of desired liquids contained in a vessel (e.g., a cuvette) or a free-space environment (e.g., a surface-tension-held environment).

More particularly the present invention presents a dual mode optical analysis system that can operate in a surface-tension-mode for spectroscopic analysis of small volumes of less that about 10 ul, while equally capable of operating to analyze large-volume samples via configured cells that can include cuvettes, Chemical Oxygen Demand (COD) cuvettes, tubes, custom made vessels, etc.

In typical operation, directed optical radiation is transmitted through a solution or suspension within either mode of the present invention and the incident light is diminished by the absorption of light by colored compounds and/or the scattering of light rays by particulate matter. Such an invention has many uses; it can be used to study pigmented molecules, to monitor the density of bacteria in a culture, and to follow the progress of an enzymatic reaction. As another beneficial example, it can be used to study a chemical analyte in an organic or inorganic medium in an industrial setting, such as for example, for environmental analysis, e.g., using COD cuvettes enables the measure of organic pollution in wastewater using the techniques and apparatus of the present invention. The main requirement is that light be absorbed or scattered by some substance in the sample under investigation.

It is known in the art that in the case of photometry or spectrophotometry, the usual quantity of interest is absorbance, A, which, for liquid samples, is most often defined as:

$$A = -\log_{10}(T) = -\log_{10}(I_R/I_0)$$

where T is the transmittance, $I_R$ the intensity (e.g., power) of light transmitted through the sample being measured and $I_0$ is the intensity of light transmitted through a blank or reference sample, which permits the cuvette based configuration as well as surface tension method of the present invention to be equally beneficial.

In either the surface tension or cuvette-based mode of operation, a user can utilize blank samples with the component being analyzed being absent and samples with the component being analyzed present to provide for the absorbance value A, which can be related to the concentration of the component being analyzed by Beer's law which states that for solutions 1 and 2:

$$\frac{A_1}{A_2} = \frac{Concentration_1}{Concentration_2}$$

Thus, when compared with a blank sample, the concentration of the component of interest being analyzed can be directly determined from the absorbance A.

Figure 1A:
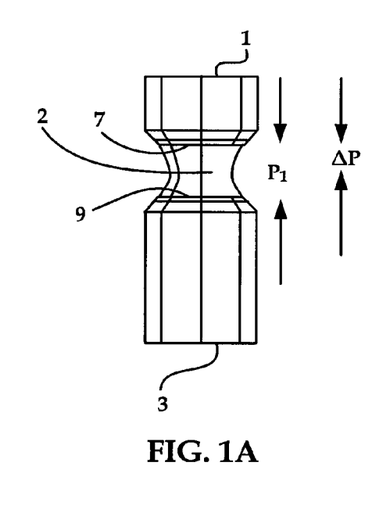
FIG. 1A and FIG. 1B show perspective views of two path lengths to illustrate the differential absorbance path length capability of the present invention.
Figure 1B:
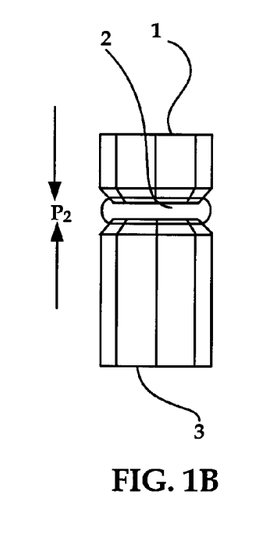

Specifically with respect to the surface-tension-mode aspect of the present invention, samples can also be measured with a differential absorbance path as shown in FIGS. 1A and 1B, and as described in incorporated by reference U.S. Pat. No. 6,628,382. Here sample absorbance can be measured by changing the optical path over which the absorbance is measured by measuring the sample at each of one or more path lengths, wherein the difference in path length combined with the difference in transmitted intensity can be used to calculate the sample absorbance. This can be of significant value if the sample is highly absorbing and the accuracy of the path difference for a small path difference can be better determined than the absolute full optical path.

Measurements in a differential mode are taken, as shown in FIG. 1A, where sample 2 is shown with a relatively long path $P_1$ and in FIG. 1B with a relatively short path length $P_2$ between the moveable pedestal or anvil-like surfaces carrying the facing surfaces 7, 9. Thus, by way of the one or more path differences ΔP, the absorbance at the shorter path $P_2$ can be subtracted from the absorbance of one or more of the longer paths to arrive at the absorbance of the sample. These path lengths are measured between two surfaces mutually facing one another, surface 7 of an upper member 1 and surface 9 of a lower member 3. During measurements, light is delivered into the sample through one of the two surfaces and the proportion of the light transmitted through the sample is collected from the sample through the other one of the surfaces. The upper and lower members may be referred to as upper and lower anvils or pedestals, respectively, but can include other platform geometries for containing a liquid sample therebetween without departing from the spirit and scope of the present invention. Thus, the difference in light path length $\Delta P(=|P2-P1|)$ may be used to calculate the optical absorbance of the sample 2 shown in FIGS. 1A-1B, since $\Delta P$ may frequently be known with a greater degree of accuracy and precision than either of $P_1$ and $P_2$.

Specifically with respect to the cuvette-mode of operation, the addition of a cuvette to a pedestal based system offers the user more versatility. Occasionally, a researcher may have a need to do certain sample types or to perform certain ancillary techniques on a sample of interest that do not lend themselves well to a container-less technique. Examples include, but are not limited to, desiring to provide measurements on a sample with an extended (low concentration) range due to longer pathlength, having a non homogenous mixture that requires a certain temperature or agitation, and/or having a diluent sample that was volatile and subject to rapid evaporation.

Accordingly, the novel integrated apparatus of the present invention provides for an instrument that can measure absorbances from about 0.005 up to about 2.0 Absorbance Units for any given pathlength via the amount of light passing through a sample in a surface-tension-held environment with sample volumes of less than about 2 $\mu$-liters (i.e. having path lengths of down to about 10 microns) or through larger sample volumes (e.g., diluted samples) of up to about 50 ml via, for example, tubes, cuvettes, COD cuvettes, custom vessels, etc., so as to result in path lengths from about 2 mm and up to about 100 mm, more often up to about 10 mm.

Beneficial aspects include the ability to make direct comparisons of the surface-tension held configuration of the present invention with the measured values provided by the integrated cuvette configuration. In particular, the present invention enables correction for differences in path lengths between the surface-tension-mode and the vessel configuration by adjustments for path lengths in the former, e.g., path lengths of down to about 10 microns, so as to equate to path lengths of up to about 1 cm or more in the latter. Moreover, another beneficial aspect of the present invention includes providing for a more-ready comparison with data from other commercial absorbance spectrophotometers that are well known by those of ordinary skill in the art.

Specific Description

Figure 2:
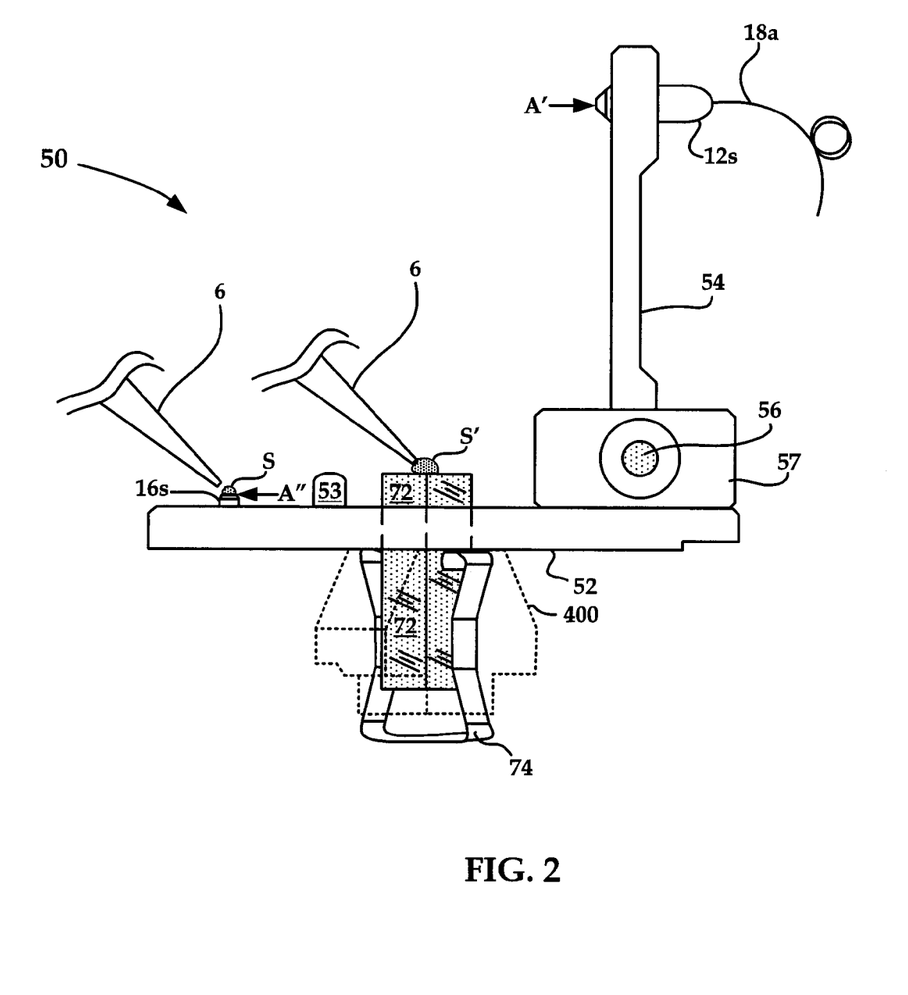
FIG. 2 is a general view of a dual mode spectrometer apparatus in the "open position".

Turning back to the drawings, FIG. 2 generally shows a side view of an example apparatus that comprises the free-space (surface-tension-method) cuvetteless based configuration integrated with a vessel (e.g., a cuvette) arrangement in accordance with disclosed aspects of the present invention.

Surface Tension Mode

In particular, with respect to the surface tension mode "cuvetteless" based aspects of the present invention, the apparatus, as illustrated in FIG. 2 and generally designated by the reference numeral 50, is shown in an "open" position in which a liquid drop analyte or reference sample, denoted by the letter S, of less than about 10 $\mu$l, more often less than about 2 $\mu$l, is dispensed or aspirated onto a lower platform surface A". As discussed in more detail below, such an "open" position enables easy access to the ends of the surfaces, e.g., surface A", which contain the liquid samples and also enables a user to easily clean such surfaces and to mount a new sample within the apparatus when desired.

Thus, in the "open position" of FIG. 2, the dispensing of a liquid sample S of less than about 10 $\mu$l, often less than about 2 $\mu$l, can often be delivery by way of a pipetting means 6, such as, but not limited to, a Finnpipette® from ThermoFisher Scientific of Waltham, Mass. The pipetted liquid is thus delivered to a lower platform A", which is often configured as a pedestal or anvil-like surface that may comprise the end of a custom or commercial SMA fiber optic connector 16s, and of which, also may in some applications, be treated with a material known by those of ordinary skill in the art to prevent over spreading of the applied liquid drop analyte or reference sample S.

Figure 3:
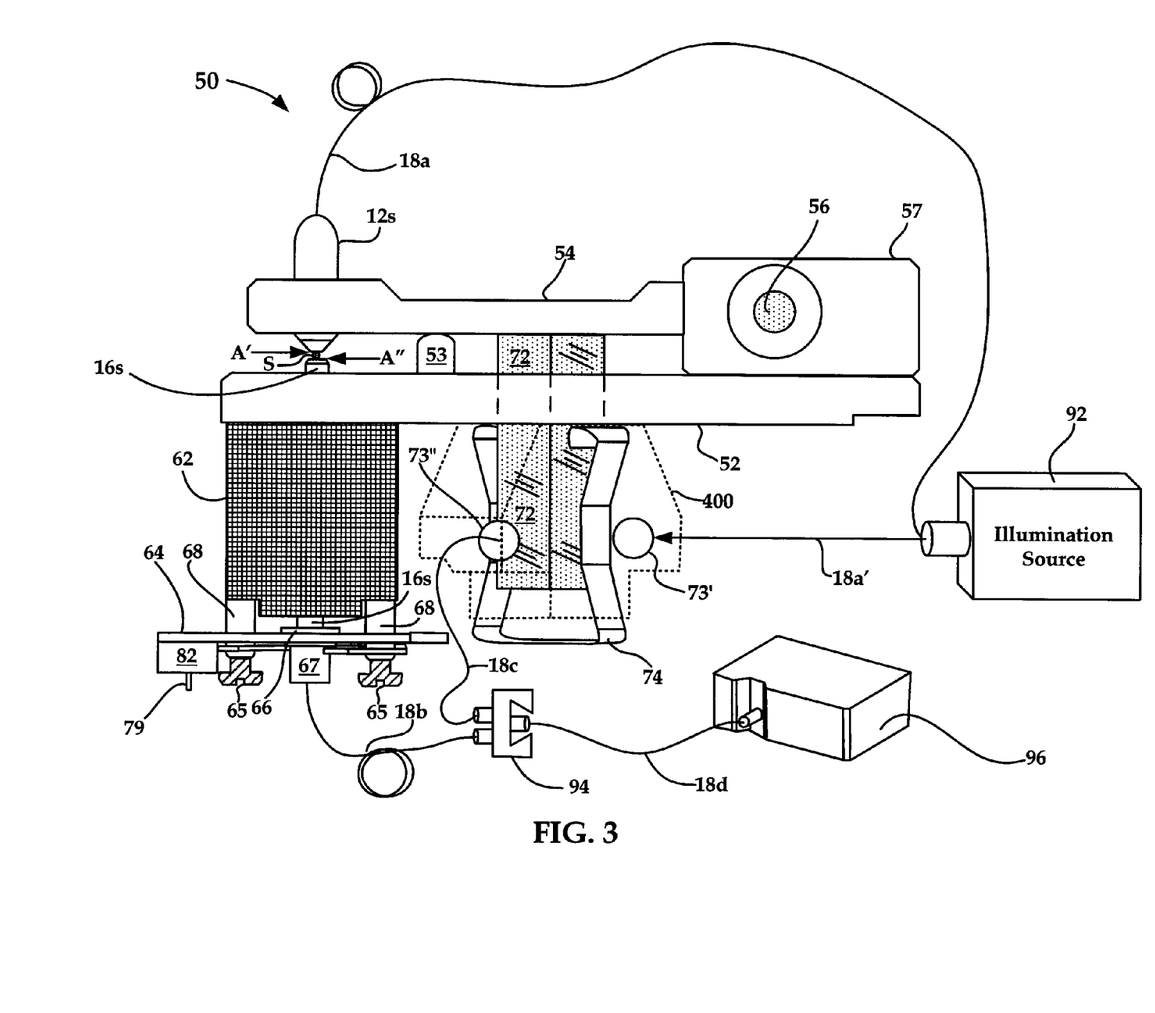
FIG. 3 is a general view of a dual mode spectrometer apparatus in the "closed position".

Thereafter, upon the application of liquid drop S, the apparatus 50, as shown in greater detail in FIG. 3, is angularly moved by a user to be in the "closed position, so as to result in the upper pedestal or anvil-like surface A', also often the end of a custom or commercial SMA fiber optic connector 12s, to be brought into contact with liquid drop sample S to capture and contain liquid drop sample S therebetween with lower surface A" in a surface tension mode.

As shown by the open position of FIG. 2 resulting in the closed position of FIG. 3, such an angular movement of the swing arm 54 is enabled by the mechanical coupling of a hinge rod 56 configured therethrough bores in both the swing arm 54 and in the hinge spacer block 57, with hinge spacer block 57 being rigidly fixed with respect to base plate 52. Accordingly, the fiber optic connector 12s, which contains surface A', and of which is mounted within and passes through a bore in swing arm 54, also angularly rotates with respect to a base plate 52 about hinge rod 56 in order to come into contact with liquid drop sample S. A stop 53 coupled to the base plate 52 and which may be in the form of a pin provides a desired position against which the lower surface of the arm 54 abuts when the arm is rotated so as to provide for the contact and measurement of liquid drop sample S, as described above.

As also illustrated in FIG. 2 and FIG. 3, a pair of optical conduits, such as, for example, an upper optical fiber 18a and a lower optical fiber 18b and disposed within respective connectors, e.g., connectors 12s and 16s, enable optical communication by way of being diametrically opposed with one another in their operating position, i.e., the "closed position" illustrated in FIG. 3.

It is to be noted that such optical conduits, e.g., optical fibers 18a and 18b, can be of any type, such as, single-mode fibers, polarization maintaining fibers, but preferably multi-mode fibers, so as to not constrain the present invention to any particular optical fiber measurement modality or limitation. As another example arrangement, the fiber ends are cleaved or polished and are often, but not necessarily, flush with the end of the fiber optic connector 12s and 16s. As another beneficial arrangement, such optical fibers 18a and 18b are coupled to one or more optical refractive surfaces (e.g., a lens (not shown)) additionally disposed within such fiber optical connectors 12s and 16s to provide for optical correction of the directed (e.g., collimation) and received (e.g., correction to the numerical aperture of the collection fiber) light so as to minimize deleterious optical losses between respective optical conduits 18a and 18b.

Turning now exclusively to FIG. 3 so as to describe the precise positioning of the surfaces A' and A" for measurement of sample S, it is to be noted that the lower optical fiber holder 16s for the lower optical fiber 18b also serves as a shaft for a linear actuator, as described in greater detail below. Although the upper optical fiber connector 12s (and consequently the coupled optical conduit fiber 18a) is fixed with respect to the swing arm 54, the lower optical fiber connector 16s (and consequently the lower optical conduit, e.g., fiber 18b) may translate, parallel to its axis (e.g., along the vertical direction), so as to enable the spacing between the two optical fibers to be varied. The base plate 52 is provided with a linear actuator that is mounted thereto so as to provide for the precise translation of the lower optical fiber connector 16s. As shown in FIG. 3, the linear actuator may comprise a motor 62 that is secured to the base plate 52 by means of fasteners 65 (such as, for instance, screws, posts, pins, rivets, etc. with or without associated bushings). The fasteners may comprise extended motor mounting screws and may pass through bushings 68 which provide a slidable mechanical engagement with a plate or board 64, as further described below.

As generally illustrated in FIG. 3, the motor is designed to produce a rotational motion of a threaded nut (not shown) which bears on a mating threaded shaft portion (not shown) of the lower optical fiber holder 16s. The lower fiber optic connector 16s replaces and/or serves as the actuator shaft of the linear actuator. The rotation of the internally threaded screw against the externally threaded shaft portion, as driven in either direction by the motor 62, causes controlled translation of the lower fiber optic connector 16s and the disposed optical conduit, e.g., 18b housed therein. The position of the lower fiber optic connector 16s may be stabilized by a plate or board 64 which is mechanically coupled to the lower fiber optic holder 16s by means of an insert ring 66. The plate or board 64 may have holes or slots (not shown) through which the bushings 68 and the fasteners, such as screws 65, pass. The fasteners 65 may comprise extended motor mounting screws. The motor 62 may be further secured to the base plate 52 by additional fasteners (not shown).

As a beneficial arrangement, the motor 62 may be a commercially available motor or linear actuator or linear translator motor. As but one example, a linear actuator motor assembly is available from Haydon Switch Instruments of Waterbury Connecticut USA as part no. 28H43-05-036. The actuator shaft of a standard off-the-shelf linear actuator or linear translator apparatus may need to be replaced by the lower fiber optic holder 16s, as described herein.

Preferably, the travel distance and/or position of the lower fiber optic holder 16s is monitored during operation of the apparatus 50, as shown in FIG. 3. As a beneficial configuration, the plate or board 64 may, in operation, be fixed to the lower fiber optic connector 16s, such that the plate or board moves together with the lower fiber optic holder. The plate or board 64 may comprise a printed circuit board (PCB) that carries electronics that perform the function of sensing movement or position of the plate or board 64. For example, the board 64 may carry an eddy current or capacitance sensor that can sense the distance of the board 64 to a back plate of the motor 62. Such eddy current sensor PCB boards are commercially available from a number of different manufacturers. The board 64 may also comprise a reference position sensor 82 that establishes a "home" or reference position when the motor control system initializes upon startup or interrupted by an opto-interrupter device 79. In addition, a collar or bushing 67 that is press fit onto a lowermost unthreaded portion of the lower fiber optic connector 16s, extending "underneath" the plate or board 64, may be added to act as a stop to prevent over-travel of the lower fiber optic holder 16s beyond its intended mechanical limits.

When the plate or board 64 is utilized as a position sensor, as described immediately above, the bushings 68 provide a slidable mechanical engagement between the holes or slots (not shown) of board 64 and the fasteners 65. Accordingly, such slots (not shown) and fasteners 65 permit translational movement of the board 64 (together with the lower fiber optic holder 16s) parallel to the axis of the lower fiber optic holder 16s but prevents rotation of the board and lower fiber optic holder with respect to the apparatus as a whole. Such rotation is undesirable as it could cause misalignment of, twisting of, light loss from or even breakage of the optical fiber contained within the lower fiber optic holder 16s.

The insert ring 66 may be either permanently or temporarily fastened to the plate or board 64. For instance, the insert ring may be permanently fastened to the plate or board with solder. Likewise, the insert ring 66 may be either permanently or temporarily fastened to the lower fiber optic holder 16s by known techniques understood by those of ordinary skill in the art. If, in operation, the lower fiber optic holder 16s and plate or board 64 moves in unison, then the insert ring 66 is fastened to both the lower fiber optic holder 16s and the plate or board 64 at least during such operation. In order to facilitate assembly or replacement of parts, it may be desirable to employ a non-permanent fastening between the lower fiber optic holder 16s and the insert ring 66, such that the lower fiber optic holder may, on occasion, be removed from the rest of the apparatus. The non-permanent fastening may comprise a tightly locked mechanical engagement between the external threads of the threaded portion (not shown) of the lower fiber optic holder 16s and internal threads of an inner hollow portion of the insert ring 66. In such a fashion, the lower fiber optic holder 16s may be held sufficiently tight in the insert ring such that it does not rotate during operation of the motor 62, yet may still be easily disengaged from the insert ring during dis-assembly.

Upon proper positioning of the surfaces A' and A" via the motor controlled mechanism(s) and sensor(s) described above, a sample column is drawn in the surface-tension-mode, wherein light is then directed through, for example, fiber optic 18a or other conventional optical means, then further directed through connector 12s, through sample S, so as to be thereafter received by fiber optic 18b. The optical light is then selected for analysis via an optical commercial or custom switch 94 so as to be thereafter coupled to a detection master commercial or custom made spectrometer 96 via a desired optical conduit, e.g., an optical fiber 18d.

The light source 92 for interrogation comprises a radiation source, such as, a xenon flash lamp or a combined deuterium arc and quartz halogen incandescent lamp commercially available from Ocean Optics, inc. p/n DT-1000). While such a commercially available source is beneficial, it is also to be understood that any source capable of delivering illumination lengths of at least about 200 nm, more often illumination wavelengths of between about 190 nm up to about 840 nm can also be utilized in the present invention when conformed to the design parameters of the present invention. In addition, depending on the light source utilized and the measurement to be made, one or more filters, such as an interference filter, can be applied so as to permit desired wavelengths of between about 190 nm up to about 840 nm. If desired, the filters can be formed into a cartridge or wheel format (not shown) to permit the ready insertion or withdrawal of such filters from designed regions of the optical path.

Moreover, the spectrometer 96, light source, 92, motor driven mechanisms, etc., are coupled to a computer driven (PC) system (not shown) having sophisticated custom or commercial software for selecting desired optical pathlengths and for choosing between the pedestal or vessel configurations, with in some cases, pre-programmed modules for common functions like DNA, RNA, and protein quantification. The data acquired, including that from a reference (or "blank") sample, can be displayed via known methods and stored for future reference, and statistical measures performed to enable a user friendly operation. As another arrangement, the software may be built in to the spectrometer 92 as opposed to the PC. As another beneficial arraignment, data can be exported to a portable storage device such as a flash drive, or even directly to a PC through a USB or wireless (Bluetooth), IEEE, Ultra-Wideband (UWB) connection.

Accordingly, the apparatus of FIGS. 2 and 3 enable a user in the surface-tension-mode to precisely control separation between an upper fiber (or other optical component) and a lower fiber (or other optical component) in order to make controlled optical absorption measurements of small quantity liquid drop analyte samples of less than about 10 µl, more often less than about 2 µl, having a path length of down to about 10µ, without the need for mechanical movement of bulky supporting parts or without the need for large sample volumes that may require dilution and cuvettes when applicable.

Vessel Mode

Turning back to the "open position" shown in FIG. 2, so as to now discuss the vessel (e.g., cuvette) based arrangement of the present invention. It is to be appreciated that when desired, i.e., when measuring large volume samples, a sample of an analyte S' or reference liquid of up to about 50 ml of solution can be disposed within a vessel 72 in order to provide an overall measurement of path-lengths of up to about 10 mm. Again the application of such an analyte S' or reference liquid can be by way of a commercial pipetting means 6 now configured to provide larger volumes of material (often the vessel 72 is filled on a lab bench (may be but not necessarily via a pipette) and then inserted into an instrument).

Such a vessel 72 is resiliently held in place via spring means 74 slidably mounted within a designed recessed portion of holder 400 (shown in phantom) that is removably affixed to the underside of base plate 52. As shown in FIG. 2 and FIG. 3, a predetermined length of vessel 72 (shown as dashed portions) is configured to pass through a designed aperture in base plate 52, wherein vessel 72 is subsequently secured as swing arm 54 angularly rotates into the "closed position," as shown in FIG. 3. In particular, upon delivery of the large volume of liquid analyte S', and after capping the vessel with an appropriate means (not shown) so as to ensure non-contamination, the swing arm 54 of apparatus 50, as shown in greater detail in FIG. 3, is again angularly moved by a user to be in the "closed position" so as to provide optical interrogation of liquid suspension/analyte S' by the system disclosed herein.

Figure 4:
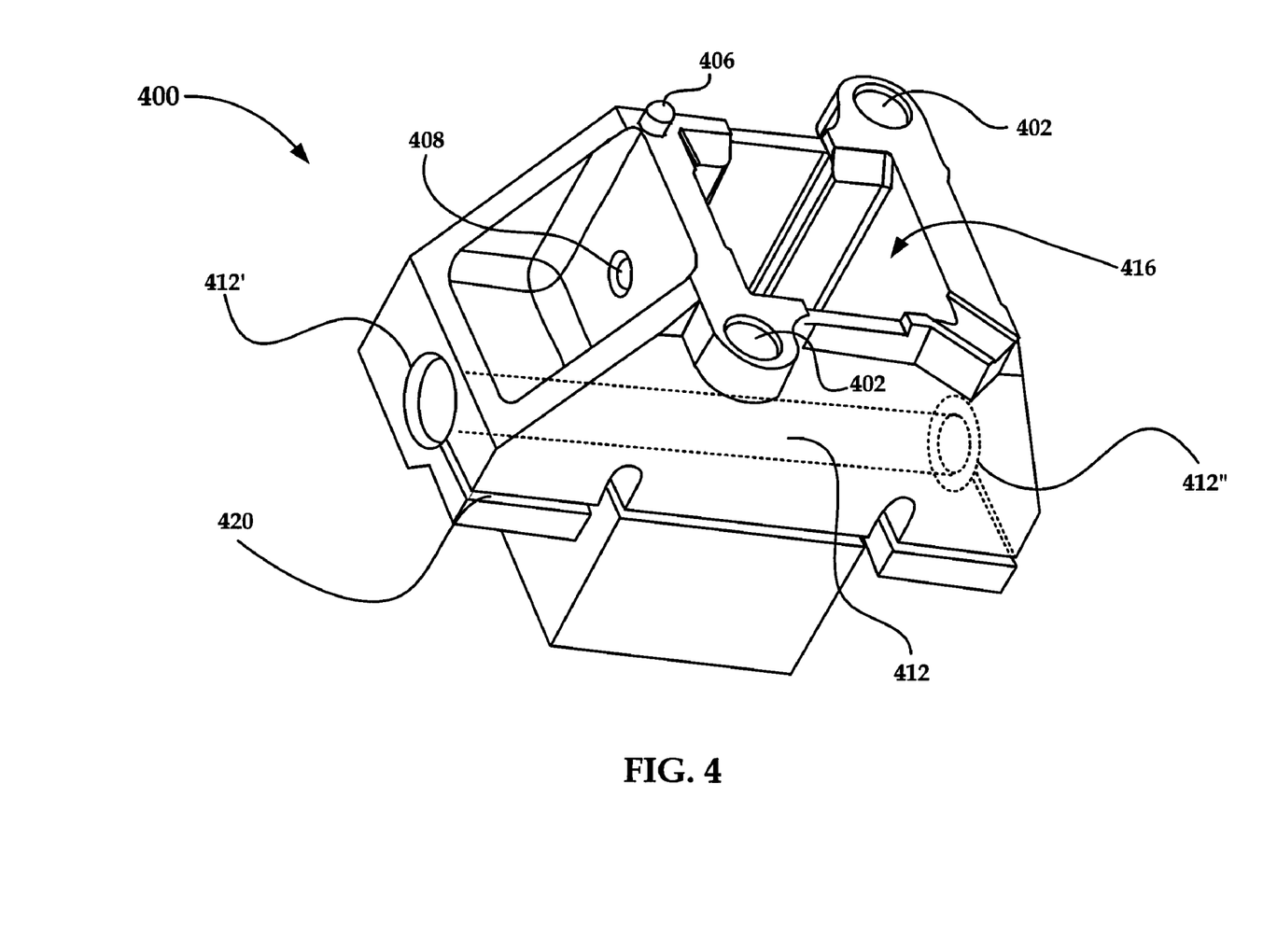
FIG. 4 illustrates an example cuvette holder capable of being configured with the dual mode spectrometer of the present invention.

FIG. 4 shows a beneficial example configuration of a vessel holder, generally designated by the reference numeral 400, of the present invention. Such a vessel holder 400 can be made of any suitable material. For example, it can be machined from metal or it can be molded from plastic, e.g., high-strength plastic. The holder so depicted in FIG. 4, is configured with coupling arrangement, such as though-holes 402, so as to be removably affixed to the bottom of the base-plate 52 shown in FIG. 2 or FIG. 3.

Such a holder further comprises an alignment pin 406 to ensure proper seating when removed for cleaning or when re-coupled if alternative mounts had been utilized. Vessel holder 400 is also formed with a transverse bore 412 (shown in phantom) so as to enable a light path to be directed through a transmissive vessel (not shown) containing a sample of interest. Transverse bore 412 (shown in phantom) in conjunction with a slotted clamping means 420 in vessel holder 400 enables a pair of optical mounts (not shown) to be mounted in counter-sunk openings 412' and 412" (shown in phantom) so as to secure predetermined transmitting and receiving optics (73' and 73," as shown in FIG. 3), e.g., refractive optics, such as ball lens, aspheres, etc.

In addition, vessel holder 400, has a recessed guiding structure 416 sized to removably accommodate a predetermined vessel (not shown) such as, a tube, or irregular shaped vessel, but often a standard cuvette as known and used in the industry. It is to be noted that often, recessed guiding structure 416 is configured to also accommodate a spring means 74, as shown in FIG. 3, to enable a sliding yet frictional fit between a predetermined vessel and the recessed guiding structure 416, whereby the vessel then fits snugly within such an opening. Preferably spring means 74 biases a desired vessel into proper alignment within recessed guiding structure 416 to enable accurate measurements. Lastly, an orifice 408, is often provided to enable insertion of a thermal controlling sensor (not shown) so as to provide temperature control of the liquid sample when desired. In addition, magnetic stirrers (not shown) can be affixed to the underside of vessel holder 400 so as to be coupled to a an associated magnetic capsule (not shown) introduced into, for example a cuvette (not shown) containing a liquid sample.

It is also to be appreciated that a vessel, such as the vessel 72 as shown in FIG. 3 in phantom, can comprises any commercial or custom made vessel, but is often a standard cuvette as exemplary shown in FIG. 3, for containing the sample S'. Such a cuvette is open at the top so as to receive liquid sample S' in the open position of FIG. 2, and is configured with a plurality of sides in a substantially predetermined parallel relationship having at least two opposing sides of optical quality capable of transmitting optical wavelengths of at least 200 nm, more often capable of transmitting optical wavelengths between about 190 nm up to about 840 nm from a desired optical illumination light source 92, as shown in FIG. 3. It is to be noted that while a standard cuvette is, as described above, is a preferable arrangement, it is to be noted that any commercial or custom rectangular cuvette (e.g., COD's) as well as other non-rectangular shaped vessels, such as tubes, and custom vessels, etc., can also be coupled into the present invention without departing from the spirit and scope of the present invention.

Chemical oxygen demand (COD), in particular, is a measure of the capacity of water to consume oxygen during the decomposition of organic matter and the oxidation of inorganic chemicals such as ammonia and nitrite. It is a quick, inexpensive means to determine organics in water, for example, waste waters or of natural waters contaminated by domestic or industrial wastes. In essence a COD test determines the amount of carbon based materials by measuring the amount of oxygen the sample will react with. The present invention thus can test the level of organics in the water photometrically (colorimetrically) by having "smart" cuvettes prepared in a COD manner known to those skilled in the art. Thus, as part of the method of operation, a water sample can be introduced into the prepared cuvette(s) and incubated with a chemical oxidant under specific conditions of temperature and for a particular period of time. Thereafter, the cuvette containing the sample is introduced into the dual mode apparatus of the present invention, as described herein, to provide colorimetric measurements enabled by the system so as to determine the level of domestic or industrial wastes in the provided sample(s).

Whatever type of vessel chosen or sample being measured, after a sample is loaded, as shown in the "open position" of FIG. 2, and readied for interrogation, as shown in the "closed position of FIG. 3, a user manipulates the coupled controls (i.e., a controlling computer system) of the present invention, as briefly described above, to perform measurements. Accordingly, as detailed in FIG. 3, light is again directed through an optical conduit, e.g., fiber optic 18a' or other conventional optical refractive, diffractive, or reflective optical means, so as to be further directed and conditioned by an optical element 73', e.g., a refractive element(s) such as a ball lens. Light, often now substantially collimated light, is then directed substantially perpendicular to a wall of vessel 72, transmitted through a liquid sample contained in vessel 72, directed out of an opposed predetermined wall of vessel 72, received by a collecting optic 73" (e.g., a designed refractive or reflective optic, often a ball lens) so as to enable a numerical aperture fit with an optical conduit, e.g., fiber optic 18c. The optical light is again selected for analysis via an optical commercial or custom switch 94. Thus, desired light to be analyzed is thereafter coupled to a detection master commercial or custom made spectrometer 96 via, as before in the surface-tension-mode, a desired optical conduit, e.g., an optical fiber 18d.

As in the surface-tension-mode, the light itself comprises a source 92, such as, a xenon flash lamp or a combined deuterium arc and quartz halogen incandescent lamp commercially available from Ocean Optics, inc. p/n DT-1000) or any source capable of delivering illumination wavelengths of at least 200 nm, more often illumination wavelengths from about 190 nm up to about 840 nm can also be utilized in the present invention when conformed to the design parameters of the present invention. Again, depending on the light source utilized and the measurement to be made, filters such as an interference filter, can be applied so as to permit desired wavelengths of between about 190 nm up to about 840 nm. If desired, the filters can be formed into a cartridge format (not shown) to permit the ready insertion or withdrawal from designed regions of the optical path.

As before, a computer driven (PC) system (not shown) having sophisticated custom or commercial software enables ease of measurement with in some cases pre-programmed modules for common functions like DNA, RNA, and protein quantification. The data acquired, including that from a reference (or "blank") sample, can be displayed via known methods and stored for future reference and statistical measures performed to enable a user friendly operation. As before, the software may either be built in to the spectrometer 92 or reside in the PC and data can be exported to a portable storage device such as a flash drive, or even directly to a PC through a USB or wireless, e.g., (Bluetooth), IEEE, and/or Ultra-Wideband (UWB) connection.

Accordingly, the apparatus of FIGS. 2 and 3 also enable a user in the vessel sampling mode to make controlled optical absorption measurements of large volumes of samples of up to about 50 ml with a preferred sample path of about 10 mm utilized for direct comparison with other commercial instruments or with the surface-tension mode measurements capable of being utilized in the same apparatus.

The discussion included in this application is intended to serve as a basic description. Although the present invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. Such modifications and the like are considered simple modifications that are well within the ability of one of ordinary skill in the art and within the scope and spirit of the invention. Accordingly, many such modifications may be made by one of ordinary skill in the art without departing from the spirit, scope and essence of the invention. Neither the description, drawings nor the terminology is intended to limit the scope of the invention—the invention is defined by the claims.

What is claimed is:

1. A dual-mode spectrophotometer for measuring an optical property of a sample, comprising:
   a first pedestal surface coupled to a first optical conduit having a transmitting end;
   a base plate;
   a second pedestal surface mechanically coupled to said base plate and configured to receive a first liquid sample, said second pedestal surface being coupled to a second optical conduit having a receiving end, wherein said second pedestal surface is further operable so as to adjust a separation between said first and said second pedestal surfaces at a variable distance (P) to pull said first liquid sample into a column so as to be contained by surface tension, thereby providing an optical path with said transmitting end of said first optical conduit and said receiving end of said second optical conduit for photometric or spectrometric measurement;
   a vessel holder configured with a recessed guide means, said vessel holder configured to be removably coupled to said base plate; and
   a sample vessel configured to be resiliently secured within said recessed guide means, said sample vessel having a second liquid sample therein and configured with at least two window means therein, thereby also providing an optical path for photometric or spectrometric measurement.

2. The dual-mode spectrophotometer of claim 1, wherein absorption measurements are provided for introduced sample volumes of less than about 2 μ-liters up to sample volumes of up to about 50 ml.

3. The dual-mode spectrophotometer of claim 1, wherein absorption measurements are provided for introduced sample volumes having said optical paths with lengths from about 10 microns up to about 100 mm.

4. The dual-mode spectrophotometer of claim 3, wherein corrections for differences in path lengths are equated to provide cross-calibration of measurements.

5. The dual-mode spectrophotometer of claim 1, wherein said dual-mode spectrophotometer is adapted to measure absorbances from about 0.005 up to about 2.0 Absorbance Units for any given pathlength.

6. The dual-mode spectrophotometer of claim 1, wherein said vessel comprises at least one vessel selected from: a rectangular cuvette, a tube, and a custom made vessel.

7. The dual-mode spectrophotometer of claim 6, wherein said rectangular cuvette comprises a Chemical Oxygen Demand (COD) sensor.

8. The dual-mode spectrophotometer of claim 1, wherein said vessel holder comprises an alignment pin to ensure proper seating when re-coupled after removal.

9. The dual-mode spectrophotometer of claim 1, wherein said vessel holder comprises a transverse bore so as to enable a light path to be directed through said vessel.

10. The dual-mode spectrophotometer of claim 9, wherein said transverse bore in conjunction with a slotted clamping means in said vessel holder enables a pair of optical mounts to be mounted in counter-sunk openings so as to secure predetermined transmitting and receiving optics.

11. The dual-mode spectrophotometer of claim 1, wherein a swing arm provided by said dual-mode spectrophotometer angularly secures said vessel.

12. The dual-mode spectrophotometer of claim 1, wherein said second pedestal is further coupled to a shaft of a linear actuator so as to enable translation of said second pedestal and provide for said variable distance (P) with respect to said first pedestal to enable differential absorbance path lengths.

13. The dual-mode spectrophotometer of claim 12, wherein said variable distance is monitored by way of an eddy current sensor that can sense a distance to a configured plate so as to enable computation of a resultant translation.

14. The dual-mode spectrophotometer of claim 12, wherein said variable distance is monitored by way of a capacitance sensor that can sense a distance to a configured plate so as to enable computation of a resultant translation.

15. The dual-mode spectrophotometer of claim 13, wherein said eddy current sensor is provided on a printed circuit board (PCB).

16. The dual-mode spectrophotometer of claim 15, wherein said printed circuit board (PCB) comprises a position sensor that establishes a reference position when a translation control system initializes upon startup or upon being interrupted by an opto-interrupter device.

17. The dual-mode spectrophotometer of claim 1, wherein said dual-mode spectrophotometer comprises an illumination source configured to provide wavelengths of at least 200 nm.

18. The dual-mode spectrophotometer of claim 1, wherein said dual-mode spectrophotometer comprises an illumination source configured to provide wavelengths from about 190 nm up to about 840 nm.

19. The dual-mode spectrophotometer of claim 1, wherein a data acquired of the photometric or spectrometric measurements can be exported to a computer based system by way of at least one wireless communication means selected from: a Bluetooth connection, an IEEE connection, and an Ultra-Wideband (UWB) connection.

20. The dual-mode spectrophotometer of claim 1, wherein said dual-mode spectrophotometer includes software configured to select one or more desired optical paths for measurement either through said first and second pedestals or said sample vessel.

21. A dual-mode spectrophotometer method for measuring an optical property of a sample contained in either a surface tension mode or contained in a cuvette, comprising:
    providing a first pedestal surface coupled to a first optical conduit having a transmitting end;
    placing a first sample on a second pedestal surface mechanically coupled to a base plate, said second pedestal surface being coupled to an optical conduit having a receiving end, wherein said second pedestal surface is further operable so as to adjust a separation between said first and said second pedestal surfaces at a variable distance (P) to pull said first liquid sample into a column so as to be contained by surface tension, thereby providing an optical path with said transmitting end of said first optical conduit and said receiving end of said second optical conduit for photometric or spectrometric measurements;
    providing a vessel holder configured with a recessed guide means, said vessel holder configured to be removably coupled to said base plate; and
    providing a sample vessel configured to be resiliently secured within said recessed guide means, said sample vessel having a second liquid sample disposed therein and configured with at least two window means therein, thereby also providing an optical path for photometric or spectrometric measurements, wherein desired photometric or spectrometric measurements can be provided on said sample held in surface tension and/or on said second liquid sample disposed therein said vessel.

22. The dual-mode spectrophotometer method of claim 21, wherein absorption measurements are provided for introduced sample volumes of less than about 2 μ-liters up to sample volumes of up to about 50 ml.

23. The dual-mode spectrophotometer method of claim 21, wherein absorption measurements are provided for introduced sample volumes having said optical paths with lengths from about 10 microns up to about 100 mm.

24. The dual-mode spectrophotometer method of claim 21, wherein corrections for differences in path lengths between said first sample being held in surface tension and said second sample being disposed in said vessel are equated to provide cross-calibration of measurements.

25. The dual-mode spectrophotometer method of claim 21, wherein said dual-mode spectrophotometer method is adapted to measure absorbances from about 0.005 up to about 2.0 Absorbance Units for any given pathlength.

26. The dual-mode spectrophotometer method of claim 21, wherein said vessel comprises at least one vessel selected from: a rectangular cuvette, a tube, and a custom made vessel.

27. The dual-mode spectrophotometer method of claim 21, wherein said rectangular cuvette comprises a Chemical Oxygen Demand (COD) sensor.

28. The dual-mode spectrophotometer method of claim 21, further comprising selecting one or more desired optical paths for measurement either through said first and second pedestals or said sample vessel.

* * * * *